US012357182B2

(12) United States Patent
Georgakoudi et al.

(10) Patent No.: US 12,357,182 B2
(45) Date of Patent: Jul. 15, 2025

(54) COLOR DEPENDENT POLARIZATION ENHANCED LAPAROSCOPY/ENDOSCOPY FOR ENHANCED VISUALIZATION OF LESIONS

(71) Applicants: Trustees of Tufts College, Medford, MA (US); Lahey Clinic, Inc., Burlington, MA (US)

(72) Inventors: Irene Georgakoudi, Winchester, MA (US); Einstein Gnanatheepam, Medford, MA (US); Robert Michael Trout, Medford, MA (US); Thomas Schnelldorfer, Arlington, MA (US)

(73) Assignees: Trustees of Tufts College, Medford, MA (US); Lahey Clinic, Inc., Burlington, MA (US)

( * ) Notice: Subject to any disclaimer, the term of this patent is extended or adjusted under 35 U.S.C. 154(b) by 167 days.

(21) Appl. No.: 18/101,294

(22) Filed: Jan. 25, 2023

(65) Prior Publication Data

US 2023/0240539 A1    Aug. 3, 2023

Related U.S. Application Data

(63) Continuation-in-part of application No. 17/284,413, filed as application No. PCT/US2019/055896 on Oct. 11, 2019, now Pat. No. 12,035,893.
(Continued)

(51) Int. Cl.
*G01J 3/44* (2006.01)
*A61B 5/00* (2006.01)
(52) U.S. Cl.
CPC .......... *A61B 5/0075* (2013.01); *A61B 5/0084* (2013.01); *A61B 5/7264* (2013.01)

(58) Field of Classification Search
CPC ... A61B 5/0075; A61B 5/0084; A61B 5/7264; A61B 1/00009; A61B 1/00096;
(Continued)

(56) References Cited

U.S. PATENT DOCUMENTS

| 5,750,994 A | * | 5/1998 | Schlager | A61B 5/1495 |
| | | | | 250/339.11 |
| 7,289,211 B1 | | 10/2007 | Walsh, Jr. et al. | |

(Continued)

FOREIGN PATENT DOCUMENTS

WO    2020077237 A1    4/2020

OTHER PUBLICATIONS

International Preliminary Report on Patentability for PCT/US2019/055896 mailed Apr. 8, 2021.
(Continued)

*Primary Examiner* — Abdullahi Nur
(74) *Attorney, Agent, or Firm* — Potomac Law Group, PLLC

(57) ABSTRACT

Methods for improved imaging of internal tissue structures, such as lesions in the peritoneum, are disclosed employing color-weighted Polarization Enhanced Light (mPEL) imaging. A target tissue can be Illuminated with light of defined polarization at a plurality of wavelengths or wavelength bands. Scattered light from the tissue is collected and its polarization states analyzed and detected either via a polarization sensitive camera or a combination or polarizing filters and a standard camera. Light detected at distinct polarization states and colors is weighted by a factor and combined to yield an image that results in optimized visualization of lesions and/or discrimination of malignant from benign lesions. The factors may be identified based on a combination of Monte Carlo simulations and regression analysis to yield enhanced sensitivity to the tissue scattering
(Continued)

power. Alternatively, the factors may be identified through machine learning based optimization algorithms to optimize tissue classification.

18 Claims, 9 Drawing Sheets

Related U.S. Application Data

(60) Provisional application No. 62/744,991, filed on Oct. 12, 2018.

(58) Field of Classification Search
CPC ..... A61B 1/00186; A61B 1/042; A61B 1/063; A61B 1/0638; A61B 1/07; A61B 1/3132
See application file for complete search history.

(56) References Cited

U.S. PATENT DOCUMENTS

| | | | |
|---|---|---|---|
| 8,125,648 B2 | 2/2012 | Milner et al. | |
| 8,634,607 B2* | 1/2014 | Levenson | G01N 21/6456 600/475 |
| 8,764,633 B2 | 7/2014 | McDowall | |
| 2002/0166971 A1* | 11/2002 | Burns | G01N 21/57 250/341.8 |
| 2003/0043476 A1 | 3/2003 | Snively et al. | |
| 2007/0185384 A1 | 8/2007 | Bayer et al. | |
| 2008/0062429 A1 | 3/2008 | Liang et al. | |
| 2008/0218727 A1* | 9/2008 | Djeziri | A61B 5/0091 356/2 |
| 2008/0249371 A1 | 10/2008 | Beckman et al. | |
| 2009/0009759 A1 | 1/2009 | Backman et al. | |
| 2011/0152625 A1 | 6/2011 | Smith | |
| 2011/0178412 A1* | 7/2011 | Orlewski | A61B 5/444 600/477 |
| 2013/0107274 A1 | 5/2013 | Vertikov et al. | |
| 2015/0018645 A1 | 1/2015 | Farkas et al. | |
| 2018/0284417 A1 | 10/2018 | Deisseroth et al. | |
| 2018/0289293 A1* | 10/2018 | Basiri | A61B 5/14552 |

OTHER PUBLICATIONS

International Search Report for PCT/US2019/055896 dated Dec. 23, 2019, 2 Pages.
Written Opinion for PCT/US2019/055896 mailed Dec. 23, 2019, 8 pages.

* cited by examiner

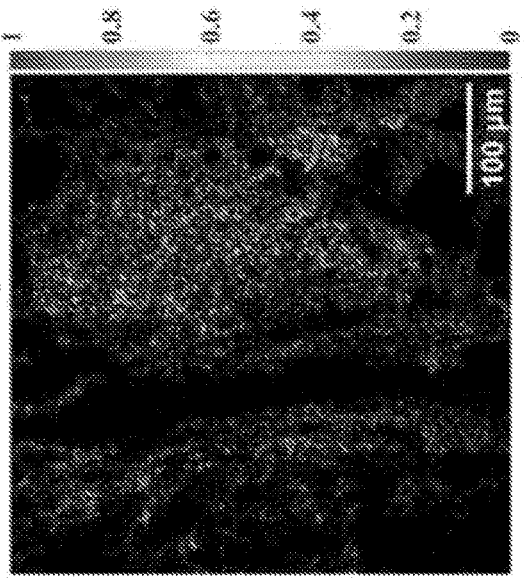
Fig. 8A Benign
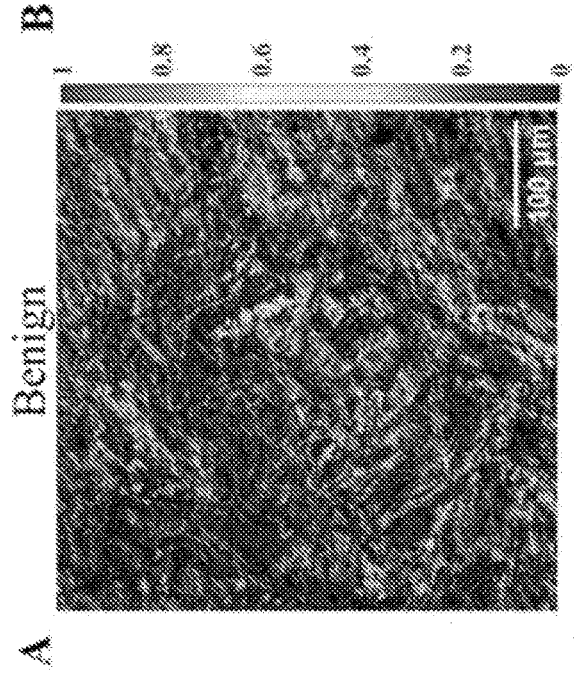
Fig. 8B Malignant
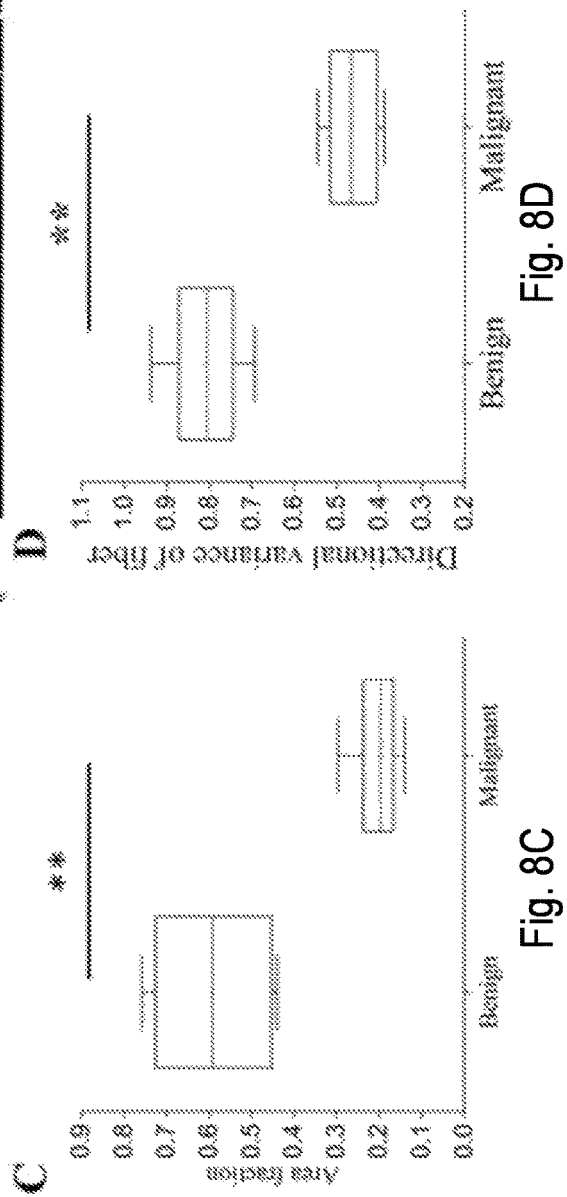
Fig. 8C
Fig. 8D Table 1: Number of lesions identified during clinical lesion detection (n=65).

| | SSL | PEL | p-value* |
|---|---|---|---|
| Seen in 1st round | 53 (82%) | 47 (72%) | 0.298 |
| Seen in 2nd round (in retrospect) | 10 (15%) | 7 (11%) | 0.604 |
| Not seen | 2 (3%) | 11 (17%) | 0.016 |

* p-value comparing both methods, Fisher's exact test

Fig. 9

COLOR DEPENDENT POLARIZATION ENHANCED LAPAROSCOPY/ENDOSCOPY FOR ENHANCED VISUALIZATION OF LESIONS

RELATED APPLICATIONS

This application is a continuation-in-part of U.S. application Ser. No. 17/284,413, filed on Apr. 9, 2021, which is a 35 U.S.C. 371 national stage of International Application No. PCT/US19/55896 filed on Oct. 11, 2019, which in turn claims priority to U.S. Provisional Patent Application No. 62/744,991 filed on Oct. 12, 2018.

GOVERNMENT SUPPORT

This invention was made with government support under grant number EB023498 awarded by the National Institutes of Health. This work was supported by the National Institute of Biomedical Imaging and Bioengineering (NIBIB R21 EB023498), and NSF Major Research Instrumentation grant 1531683. The government has certain rights in the invention.

TECHNICAL FIELD

The present invention relates generally to operative and non-invasive imaging, such as laparoscopy, thoracoscopy, arthroscopy, and endoscopy, for detecting occult tissue abnormalities, such as neoplasms, cancer metastases, fibrosis, arthritis, wound healing, and endometriosis. Further, the present disclosure relates to multi-wavelength polarization enhanced light (PEL) imaging systems and methods, which can be used to detect lesions (e.g., peritoneal lesions) as well as distinguish between benign and malignant lesions.

BACKGROUND

For cancer patients, prognosis and treatment selection fundamentally rely on the staging assessment of the underlying cancer, e.g., determining the absence or presence of distant metastases. Despite improvements in the available staging tools, including cross-sectional radiographic imaging and laparoscopy, the accuracy of staging for gastrointestinal and gynecologic malignancies varies tremendously, with "under-staging" considered as a common problem. Up to 30% of patients with these malignancies have distant recurrence of cancer after major resections with curative intent.

In the United States alone, this "understaging" problem is estimated to be about 15,000 patients per year. Metastatic recurrences of cancer, which often occur on the surface of the peritoneum, are thought to arise from the inability of conventional methods to detect small metastases (typically less than 3 mm in size) during initial staging. Although promising new therapies for metastatic cancers are in development, the inability to detect early stage metastases can delay or compromise further treatment options.

The current intraoperative standard applied to screen for peritoneal metastases is the deployment of a laparoscope that pierces the abdominal wall to permit visual inspection of the peritoneum. Unfortunately, utilizing current laparoscopic imaging techniques, the sensitivity with which a clinician can identify the presence of these lesions is unsatisfactory, with false negative rates reportedly as high as 36 percent. The tendency of illuminating light to penetrate into the tissue beyond clinically relevant depths before returning to the collection aperture of the laparoscope results in images that often lack sufficient clarity to identify tissue abnormalities localized to the tissue surface, including metastatic lesions.

Polarization Enhanced Light (PEL) imaging has been proposed for various biomedical applications as a way of improving surface image contrast. Generally speaking, PEL imaging allows one to distinguish light that has been singly-scattered from a tissue surface from light that has undergone numerous scattering events deeper in tissue, thereby providing an enhanced surface image.

However, despite this potential advantage in surface imaging, PEL techniques have not been generally adopted for laparoscopy. It has proven difficult to incorporate the necessary polarizing structures into conventional laparoscopes. Accordingly, there exists a need for better laparoscopic imaging systems and better methods for detecting tissue abnormalities.

SUMMARY

Aspects of the present disclosure address the above-referenced problems and/or others.

Methods and apparatus for improved imaging of internal tissue structures, such as metastatic cancer lesions in the peritoneum, are disclosed, which employ polarization enhanced light (PEL) imaging and in particular multi-wavelength PEL imaging. In comparison to conventional imaging, it has been found that substantially increased contrast of tissue surface features can be achieved with PEL imaging, particularly color PEL imaging. Methods are also disclosed for enhancing PEL imaging utilizing white light or distinct wavelength bands for illumination and color charge coupled devices (color CCDs) for detection.

In one aspect, a method for improved visualization of lesions using an optical imaging device (e.g., an endoscope, a laparoscope, a colposcope, among others) is disclosed, which employs differential weighting of signals detected in different wavelength channels when performing PEL imaging. As discussed in more detail herein, during PEL, a target tissue is illuminated by linearly polarized light and light backscattered from the illuminated target tissue is collected along both the co- and cross-polarized orientations. The difference between such two backscattered images is referred to as a PEL image. In embodiments of the present teachings, backscattered light at a plurality of wavelengths is detected to generate a plurality of backscattered detection signals with each corresponding to one of the illuminating wavelengths or wavelength bands (colors). Wavelength-dependent weighting factors are applied to the backscattered detection signals, e.g., to augment the detection sensitivity of PEL, for example, to obtain enhanced visualization of lesions, if any, in a target tissue.

In embodiments, the weighting factors can be determined using computational models, or can be empirically determined via exploring a space of plausible weighting factors. By way of example, and without limitation, such computational models can include machine learning models and Monte Carlo based models. By way of example, a polarization-sensitive Monte Carlo simulation for a single layered tissue model can be used to compute polarized light propagation in tissue with similar optical properties to those of peritoneal tissue. The expected red, green, and blue (RGB) signal values can be derived from the simulated reflectance spectra by considering detector efficiency profiles of digital cameras suitable for use in obtaining the images. Multiple regression analysis with simulated data sets for a range of scattering and absorption properties can be utilized to derive a regression equation for the scattering power of the target tissue based on differentially-polarized images acquired in each wavelength channel. In various embodiments, the resulting weighting factors can be applied to images obtained from patients who had undergone staging laparoscopy for gastrointestinal malignancies. The use of the regression equation can not only result in enhanced lesion detection but can also improve discrimination of malignant and benign lesions.

In one aspect, a method of laparoscopic, thoracoscopic, or endoscopic examination of a target tissue region is disclosed, which comprises illuminating a target tissue region with illuminating radiation having a first defined polarization and having a plurality of wavelengths, detecting radiation backscattered from the illuminated target tissue in response to illumination by said illuminating radiation and generating a plurality of detection signals each corresponding to one of said wavelengths, applying wavelength-dependent weighting factors to said detection signals to generate a plurality of weighted detection signals, and utilizing said weighted detection signals to compute scattering power of said target tissue. In some embodiments, a single broadband light source can be utilized to generate the polarized illuminating radiation having a plurality of wavelengths. In some other embodiments, multiple monochromatic light sources generating radiation with a common defined polarization but at different wavelengths or wavelength bands can be utilized to generate the illuminating radiation.

Further, the computed scattering power can be utilized to assess the target tissue for presence of a lesion. Further, the scattering power can be utilized to assess whether a lesion is a benign or a malignant lesion.

The wavelength-dependent weighting factors can be acquired empirically or based on a theoretical simulation, e.g., based on any of machine learning and Monte Carlo simulation.

In one aspect of the invention, optical systems are disclosed including a laparoscope having an optical input port for receiving illuminating radiation, at least one optical illumination waveguide (e.g., fiber optic or lens rod) for directing the illuminating radiation from the input port to a distal end of the waveguide, and an optical collection waveguide having a distal end aperture for collecting backscattered radiation from the tissue region and further having a proximal end for transmitting the backscattered radiation to a detector, the detector and optical collection waveguide defining an optical return path. The system can further include a polarizer positioned at the distal end of the illumination waveguide configured to polarize the illuminating radiation and direct polarized illuminating radiation onto a target tissue region to be examined, at least one lens disposed in the optical return path for imaging the tissue region unto the detector, and a second analyzing polarizer also disposed in the optical return path, whereby backscattered radiation of distinct polarizations can be passed to the detector. In certain embodiments, the lens can advantageously be an adjustable focus or zoom lens. Moreover, in some embodiments, the system can further include a variable wavelength retarder (also referred to as a variable waveplate) also disposed in the optical return path to facilitate serial acquisition of two or more images of differing polarization. Alternatively, in another embodiment a CCD camera can be incorporated into distal end optics along with appropriate analyzer filters. In yet other embodiments, a polarization sensitive camera can be utilized for acquisition of images at different polarizations.

In yet another aspect of the invention, methods are disclosed for significantly improving the staging accuracy of peritoneal laparoscopy by increasing its capacity to detect such small, occult metastases. Polarization-gating is employed to highlight surface features, and thereby increase the detection sensitivity for superficial peritoneal metastases. In one embodiment, polarized radiation can be used to illuminate the target tissue region. Scattered radiation co- and cross-polarized relative to the polarization of the illumination radiation can be detected. A differential signal corresponding to a difference between the intensities of the detected scattered radiation at those two polarizations can be analyzed to derive information about tissue structure and/or detect abnormalities. This analysis can be performed at two or more different wavelengths (or wavelength bands) or with white light illumination and color images obtained via a multi-pixel color detector.

In a related aspect, a method of laparoscopic, thoracoscopic, or endoscopic examination of a target tissue region is disclosed, which comprises illuminating a target tissue region with illuminating radiation having a first defined polarization and having a plurality of wavelengths, and detecting radiation backscattered from the illuminated target tissue in response to illumination by the illuminating radiation and generating a plurality of detection signals each corresponding to one of the wavelengths. A plurality of wavelength-dependent weighting factors can be applied to the detection signals to generate a plurality of weighted detection signals. The weighted detection signals can be utilized to compute an image of the target tissue.

In various embodiments, the image of the target tissue can be utilized to assess the target tissue for presence of a malignant lesion. By way of example, the weighted detection signals can be employed to compute a scattering power of the target tissue. The scattering power of the target tissue can be in turn utilized to assess the target tissue for presence of a malignant lesion. For example, a lesion identified in the target tissue can be classified as a malignant lesion when the computed scattering power is greater than a predefined threshold.

By way of example, the wavelength-dependent weighing factors can be determined based on any of machine learning or Monte Carlo simulation. By way of example, and without limitation, some examples of suitable machine learning methods include random forest, logistic regression, deep learning methods, such as convolutional neural networks or generative adversarial networks.

In some embodiments, the detection of the backscattered radiation at each of the wavelengths includes generating a first detection signal corresponding to a polarization of the backscattered radiation parallel to said first polarization (i.e., the polarization of the illuminating radiation) and a second detection signal corresponding to a second polarization of the backscattered radiation perpendicular to said first polarization. The method further includes processing the first and second detection signals to generate, for each of the wavelengths, a surface signal associated with a superficial portion of the illuminated target tissue. The surface signals associated with the wavelengths can be utilized to compute a scattering power of the superficial portion of the target tissue.

In some embodiments, the scattering power can be computed as a weighted average of the surface signals associated with said wavelengths. In some such embodiments, a weighing factor corresponding to each of the wavelength-dependent surface signals is computed using Monte Carlo simulation and multiple regression.

In a related aspect, a method of laparoscopic, thoracoscopic, or endoscopic examination of a target tissue region is disclosed, which includes illuminating a target tissue region with radiation having a first defined polarization and having a plurality of wavelengths, detecting radiation backscattered from the illuminated target tissue in response to illumination by the illuminating radiation and generating a plurality of detection signals each corresponding to one of the wavelengths. A plurality of wavelength-dependent weighting factors can be applied to the detection signals to generate a plurality of weighted detection signals and the weighted detection signals can be employed to generate an indicator that can indicate whether a malignant lesion is present in the target tissue.

By way of example, the indicator can indicate a scattering power of the target tissue. By way of example, in some such embodiments, the scattering power can be compared with a predefined threshold to determine whether a lesion is present and/or a detected lesion is malignant. For example, a lesion may be identified as malignant when the tissue scattering power is greater than the threshold.

The scattering power can be computed, for example, as a weighted average of the detection signals at the plurality of wavelengths.

In some embodiments, the step of detecting the backscattered radiation at each of the wavelengths comprises generating a first detection signal corresponding to a polarization of the backscattered radiation parallel to said first polarization (i.e., the polarization of the illuminating radiation) and generating a second detection signal corresponding to a second polarization of the backscattered radiation (i.e., a polarization different than the polarization of the illuminating radiation, e.g., a polarization perpendicular to the polarization of the illuminating radiation). The first and the second detection signals can be processed to generate, for each of the wavelengths, a surface signal associated with a superficial portion of the illuminated target tissue. For example, for each wavelength, the second detection signal (i.e., the signal corresponding to the perpendicular polarization) may be subtracted from the first detection signal (i.e., the signal corresponding to the parallel polarization) to generate the surface signal. The surface signals associated with the wavelengths can be utilized to compute a scattering power of the superficial portion of the target tissue. By way of example, the scattering power can be computed as a weighted average of the wavelength-dependent surface signals, where the weighting factors can be determined either empirically or theoretically, e.g., via Monte Carlo simulation.

Further understanding of various aspects of the present teachings can be obtained by reference to the following detailed description in conjunction with the drawings, which are described briefly below.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which:

FIG. 8A depicts 2D variance of collagen fibers of malignant lesions;

FIG. 8B depicts 2D variance of collagen fibers of benign lesions;

FIG. 8C depicts box plots of volume fraction and mean directional variance fibers;

FIG. 8D depicts a box plot of volume fraction for malignant and benign lesions; and FIG. 9 is a table of a number of lesions identified during clinical lesion detection.

DETAILED DESCRIPTION

Figure 1:
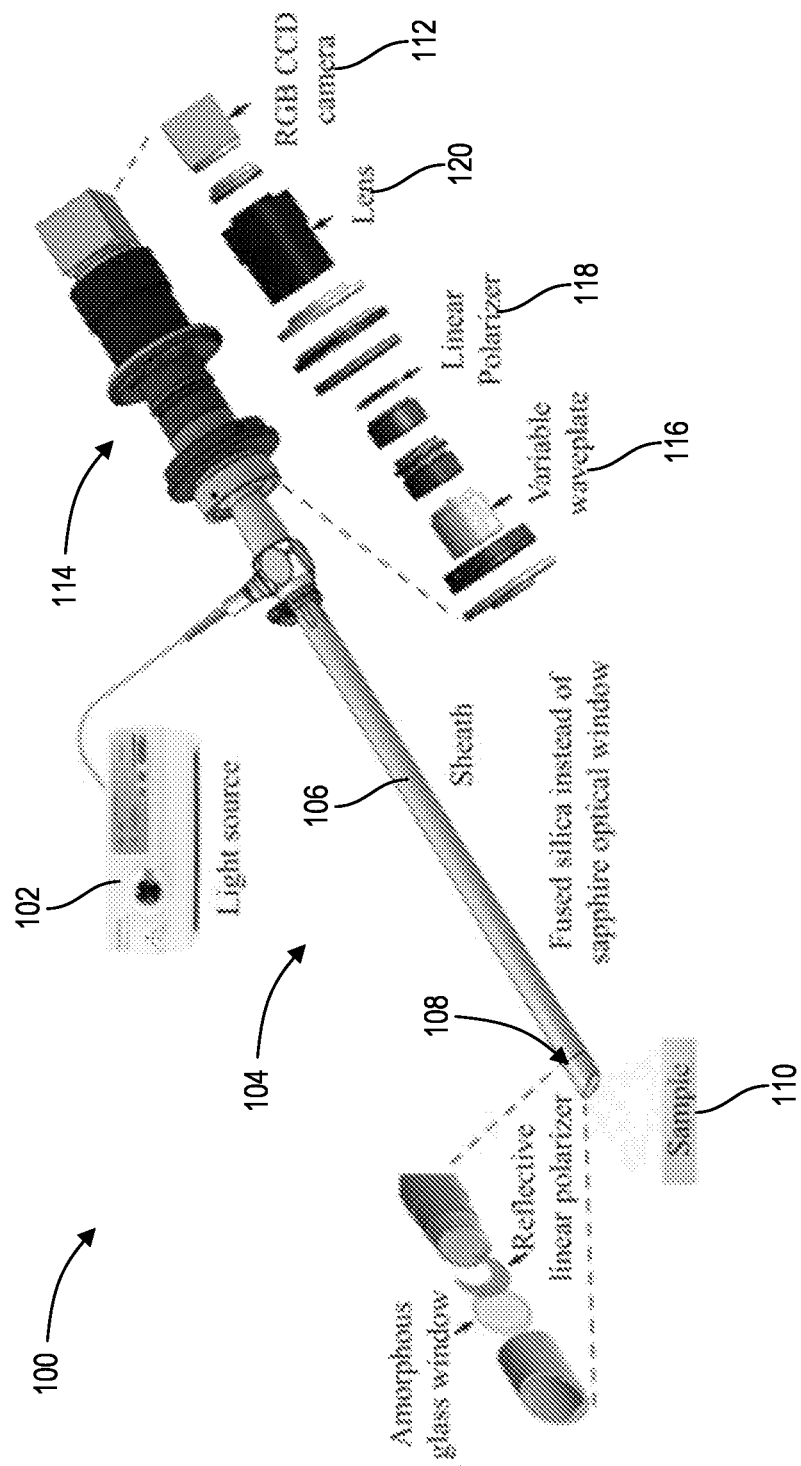
FIG. 1 schematically depicts a device that employs color-weighted Polarization Enhanced Light imaging (mPEL) device with proximal optical assembly and distal cap components in accordance with an exemplary embodiment.

Successful treatment of cancers requires optimal selection of treatment modalities. Surgical resection is a common treatment modality for treatment of various cancers and is clinically utilized in almost half of all cancer patients.

The appropriateness of surgical resection is typically determined by the extent of the cancer (i.e., staging). Despite careful preoperative radiographic and intra-operative evaluation, the accuracy of staging for distant metastases remains poor, as demonstrated by a significant rate of early cancer recurrence in patients who underwent a "complete" operative resection for many types of cancers. It is therefore desirable to develop an imaging system that will enhance the visibility of these occult and presumed small distant metastases, i.e., increase their optical contrast.

Current intraoperative evaluation of peritoneal metastases relies on white light-based standard laparoscopy during routine abdominal cancer operation. However, significant limitations still exist in the use of white light for peritoneal metastasis detection. Chief among these are poor sensitivity to lesions smaller than a few millimeters, and reduced specificity due to benign fibrotic changes, which appear similar to malignant metastases.

The terms "laparoscope" and "laparoscopic" as used herein are intended to generally encompass instruments, such as conventional laparoscopes as well as thoracoscopes, arthroscopes, bronchoscopes, colonoscopes, cystoscopes, endoscopes, entereroscopes, hysteroscopes, laryngoscope, mediastinoscopes, sigmoidoscopes, pleuroscopes, esophagoscopes, and ureteroscopes, that can perform diagnostic, minimally invasive diagnostic or therapeutic tasks by insertion either into a body orifice or by small incisions to access internal tissue.

The term "about" as used herein denotes a variation of at most 10% around a numerical value.

The phrase "a superficial portion of a target tissue" refers to portion of the target tissue that extends from a surface of the target tissue to a depth in a range of about 100 microns to about 300 microns below the surface.

In one aspect, the present teachings provide methods and systems for laparoscopic, thoracoscopic, or endoscopic examination of a target tissue region by illuminating the target tissue with polarized radiation (light) at multiple wavelengths (e.g., illuminating the target tissue with linearly polarized white light), detecting light scattered from the target tissue in response to the illumination, and generating detection signals (e.g., images of the target tissue) each corresponding to one of those wavelengths or wavelength bands. Wavelength-dependent weighting factors can be applied to the detection signals (e.g., to the images obtained at different wavelengths) and the weighted signals can be utilized, e.g., via construction of a regression relation as discussed herein, to detect lesions and to discriminate between benign and malignant lesions.

When target tissue is illuminated with linearly polarized light, reflected light is received from both the surface and the bulk of the tissue. Reflectance originating from deeper within the sample follows a longer optical path and becomes randomly polarized. In contrast, the surface reflectance from biological tissues predominantly retains the direction of the incident polarization, and is mostly co-polarized to the illumination radiation.

The distinction between the polarization states of the surface and bulk signals is exploited in differentially polarized light imaging in order to remove the bulk signal, leaving the surface signal. In one embodiment, the reflectance is examined through a linear polarizer (also referred to as an analyzer) in two configurations. In the first of these configurations, the linear polarizer is oriented parallel to the illumination polarization, passing the surface signal ($I_{surface}$), and half of the depolarized bulk signal ($I_{bulk}$). Next, the linear polarizer is oriented perpendicular to the illumination polarization, blocking the majority of the surface signal, while again passing half of the bulk signal. In some embodiments, a polarization sensitive camera can be utilized in which such differential polarization detection functionality is integrated.

Thus, the total intensity of the parallel-polarized reflectance, Ipar, is the sum of the surface signal and half of the bulk signal, whereas the perpendicular polarized signal is composed only of half the bulk signal. With this, it is possible to separately image the sample in both parallel and perpendicular linear polarizer configurations. The perpendicular image Iper may then be arithmetically subtracted from the parallel image to produce a difference image limited to signal received from the surface reflectance:

$$Ipar = Isurface + \tfrac{1}{2} Ibulk$$

$$Iper = \tfrac{1}{2} Ibulk$$

$$Ipar - Iper = Isurface$$

In some embodiments, the present teachings can be employed not only to detect lesions but also to distinguish between benign and malignant lesions (e.g., peritoneal lesions). Since peritoneal lesions are predominantly superficial and involve significant disruptions in the structure and organization of the extracellular stroma of "healthy" peritoneal tissue, the scattering cross section of malignant tissue is relatively lower than that of the surrounding background tissue and benign fibrosis.

In this regard, in embodiments, 'scattering power' rather than 'scattering coefficient' can be used to identify malignant lesions. In principle, the tissue scattering coefficient can be approximated by $\sim\lambda^{-b}$, where $\lambda$ denotes the wavelength of the illuminating radiation, and b is defined as the scattering power. In some embodiments, a Monte Carlo-based regression analysis can be performed to extract the general scattering power dependence on several different wavelength channels associated with the scattered radiation. For example, the Monte Carlo-based regression analysis can be performed on three RGB color channels of the differential polarization images, e.g., utilizing a regression relation among the color images, as described further herein.

Since scattering cross section of tumor tissue is generally lower than that of the surrounding tissue, and scattering power is inversely proportional to scattering cross section, lesions can exhibit a greater scattering power than the background tissue resulting in a positive Weber contrast.

By way of example, white light (WLL) and differential polarization laparoscope (PEL) images can be computed, respectively, as the sum and difference of co- and cross-polarized signals:

$$WLL = I_{surface} + I_{deep} = (R_{\|} + R_{\perp}) + (G_{\|} + G_{\perp}) + (B_{\|} + B_{\perp}) \quad (1)$$

$$DPL = I_{surface} = (B_{\|} - R_{\perp}) + (G_{\|} - G_{\perp}) + (B_{\|} - B_{\perp}) \quad (2)$$

where R, G, B refer to red, green, and blue components of white light respectively and the ∥, ⊥ subscripts refer to co- and cross-polarized components of light, respectively. The Monte Carlo based regression analysis can establish an empirical equation for scattering power of superficial tissue in the form of weighted differential polarization images.

In some embodiments, a Monte Carlo based regression analysis can be utilized to establish an empirical equation for the scattering power (b) of superficial tissue in the form of weighted differential polarization images as follows:

$$b = a_0 + a_1(R_{\|} - R_{\perp}) + a_2(G_{\|} - G_{\perp}) + a_3(B_{\|} - B_{\perp}) \quad (3)$$

The regression coefficients $a_i$ (i=0, 1, 2, 3), which represent the contributions of RGB values to scattering power, can be estimated, for example, based on multiple regression of the Monte Carlo simulated values.

The above multicolor analysis of scattering data acquired via illumination of a target tissue may result in the following relation for assessment of the target tissue based on color dependence of PEL (mPEL):

$$mPEL = 0.4705 - 0.0073(R_{\|} - R_{\perp}) - 0.0039(G_{\|} - G_{\perp}) + 0.1104(B_{\|} - B_{\perp}) \quad (4)$$

It was found that in the example for which the above relation was derived, the above relation was shown to exhibit better correlation to scattering power than differential polarized light signal without weighting factors and owing to this characteristic the proposed relation has the potential of use in improved staging of lesions. The computed relation was applied to images obtained from patients who underwent staging laparoscopy for gastrointestinal malignancies, and it was observed that the proposed relation not only enhanced lesion detection but also improved discrimination of malignant and benign lesions.

In other embodiments, a plurality of different combinations of color and polarization dependent images can be considered to identify a subset that can yield an optimal classification. By way of example, in some embodiments, machine learning techniques can be used to identify such optimal combination. By way of example, in some such embodiments, the parameter mPEL can be defined according to the following relations (other parameters are defined as above):

$$mPEL = |a_1(g_\| - g_\perp) - a_2(b_\| - b_\perp)| - a_3|g_\perp - b_\perp|$$

$$mPEL = |(a_1 g_\| - a_2 g_\perp) - a_3(a_4 b_\| - a_5 b_\perp)| - a_6|a_7 g_\perp - a_8 b_\perp|$$

$$mPEL = a_1\left(\frac{g_\| - a_2 g_\perp}{b_\| - a_3 b_\perp}\right) - a_4\left(\frac{g_\perp}{b_\perp}\right)$$

Referring now to FIG. 1, a laparoscopic system 100 is shown in accordance with an exemplary embodiment. In this embodiment, the laparoscopic system 100 includes an illuminating light source 102 and a laparoscope 104. The light source 102 couples to the laparoscope 104 at an optical input port and delivers light to the laparoscope 104. In some embodiments, the light source 102 can include a plurality of polarized monochromatic or narrow band light sources each of which can provide light at a different wavelength or wavelength band (e.g., red, blue or green). In some embodiments, the light source 102 can provide polarized white light.

The laparoscope 104 includes an ~30 cm long metal tube 106 that contains an optical fiber. Together the tube 106 and the optical fiber may be referred to as an optical illumination waveguide. The optical fiber extends from proximal end of the metal tube 106 to a distal end of the tube 106 and is connected to and in optical communication with the light source 102. In some embodiments, the laparoscope 104 further includes a first or distal polarizer 108 (e.g., a linear polarizer) positioned at the distal end of the tube 106. The distal polarizer 108 is configured to polarize the light provided by the light source 102 and carried by the optical fiber and is configured to direct the polarized light onto a target region (or sample region) 110 that is undergoing examination. The target region 110 scatters the light provided by the laparoscope 104. In some embodiments, the laparoscope 104 further includes a gradient index (GRIN) lens that receives the backscattered illumination and relays it to the proximal end of the laparoscope 104.

The laparoscope 104 can further include an optical collection waveguide with a distal end aperture for collecting the backscattered light from the target region 110. The optical collection waveguide is connected to and is in optical communication with a detector 112 (e.g., an optical camera). The optical collection waveguide is configured to transmit the backscattered light to the detector 112. Together, the optical collection waveguide and the detector 112 define an optical return path.

In some embodiments, the laparoscope 104 includes an adapter 114 disposed between the detector 112 and the tube 106. The adapter 114 can include a variable waveplate 116, a second or proximal polarizer 118 (e.g., a linear polarizer), and a lens 120. The variable waveplate 116 and the polarizer 118 receive the backscattered light and depending on the state of the variable waveplate 116 either the parallel or perpendicular component of the backscattered light passes through the waveplate 116 and the polarizer 118. The use of an electrically controlled variable waveplate 116 enables rapid switching between the parallel and perpendicular components of the backscattered light, thereby facilitating serial acquisition of two or more images of differing polarization for video-rate acquisition. The backscattered light that passes through the waveplate 116 and the polarizer 118 is then focused by the lens 120. In some embodiments, the lens 120 is an adjustable focus or zoom lens that focuses the received backscattered light onto the detector 112.

In some embodiments, the detector 112 includes an RGB camera. The CCD arrays used by these types of cameras are covered by a great number of red, green, and blue color filters in an arrangement referred to as Bayer tiling. The signal read from this array forms the raw Bayer-tiled image, which is then read by a color processing algorithm to produce the final image. Depending on the algorithm applied, the resulting image may be in RGB color or in monochrome. In the former case, for every pixel in the array, a red, green, and blue intensity value is extrapolated from neighboring color pixels and the pixel itself, creating an image with the same spatial resolution as the raw Bayer tile array, but where each pixel has a red, green, and blue value associated with it instead of just its filter's color. In the monochrome case, a single intensity value is calculated for each pixel as the weighted average of the three-color intensities in the local area.

In either case, the intensity values for each pixel can be recorded by the camera. In some embodiments, the camera can have a greater intensity resolution than an 8-bit resolution typically applied in laparoscopes to accommodate PEL signals that are generally at least an order of magnitude weaker than a signal associated with the total reflectance. Thus, in various embodiments, to effectively resolve such signals, a greater intensity resolution than that typically employed in regular endoscopic reflectance imaging is employed. Following the collection of the parallel and perpendicular polarized images, each of the corresponding intensity values in the perpendicular image is subtracted from its corresponding value in the parallel image in software. This is straightforward for monochrome images, where corresponding subtracted pixels share the same position, and only slightly more complicated for RGB images. For RGB images, the raw Bayer-tiled image is recorded without any of the camera's color-processing algorithms applied to avoid any potential artifacts that may be introduced when applied prior to subtraction (this mostly concerns automatically applied color correction). The images are then subtracted from one another in the same manner as in the monochrome case, after which an RGB color image is generated from the Bayer-tiled difference image via a simple linear color processing algorithm without correction.

The ability of the system to image in RGB provides additional practical information beyond what is gleaned in monochrome. It allows the system to meet not only the original capabilities of conventional non-polarizing laparoscopes, which image in RGB color, but also provide useful information, such as a more clear resolution of lesions than typically feasible using conventional techniques, via spectral information provided by the three color channels. Moreover, as discussed further herein, wavelength-dependent weighting factors can be applied to images associated with different colors and the weighted images can be utilized to detect lesions and to discriminate between benign and malignant lesions.

The designs disclosed herein are only a few of the possible configurations capable of PEL imaging. Alternatives include the use of two cameras and a combination of optical elements that separates the parallel and perpendicular components of the backscattered/reflected light and directs each to its own camera. The advantage to having such a two-camera system relative to a singular one is that given all the cameras used here have the same max frame rate, a two-camera system would be able to stream PEL images at this max frame rate, while a single camera system would only be able to do so at half this frame rate. This follows from the single camera having to image two frames (parallel and perpendicular) for every PEL frame produced, while in the two-camera setup each of these two component frames is collected by a separate camera, allowing the resulting PEL image stream to be collected at the full framerate.

Figure 2:
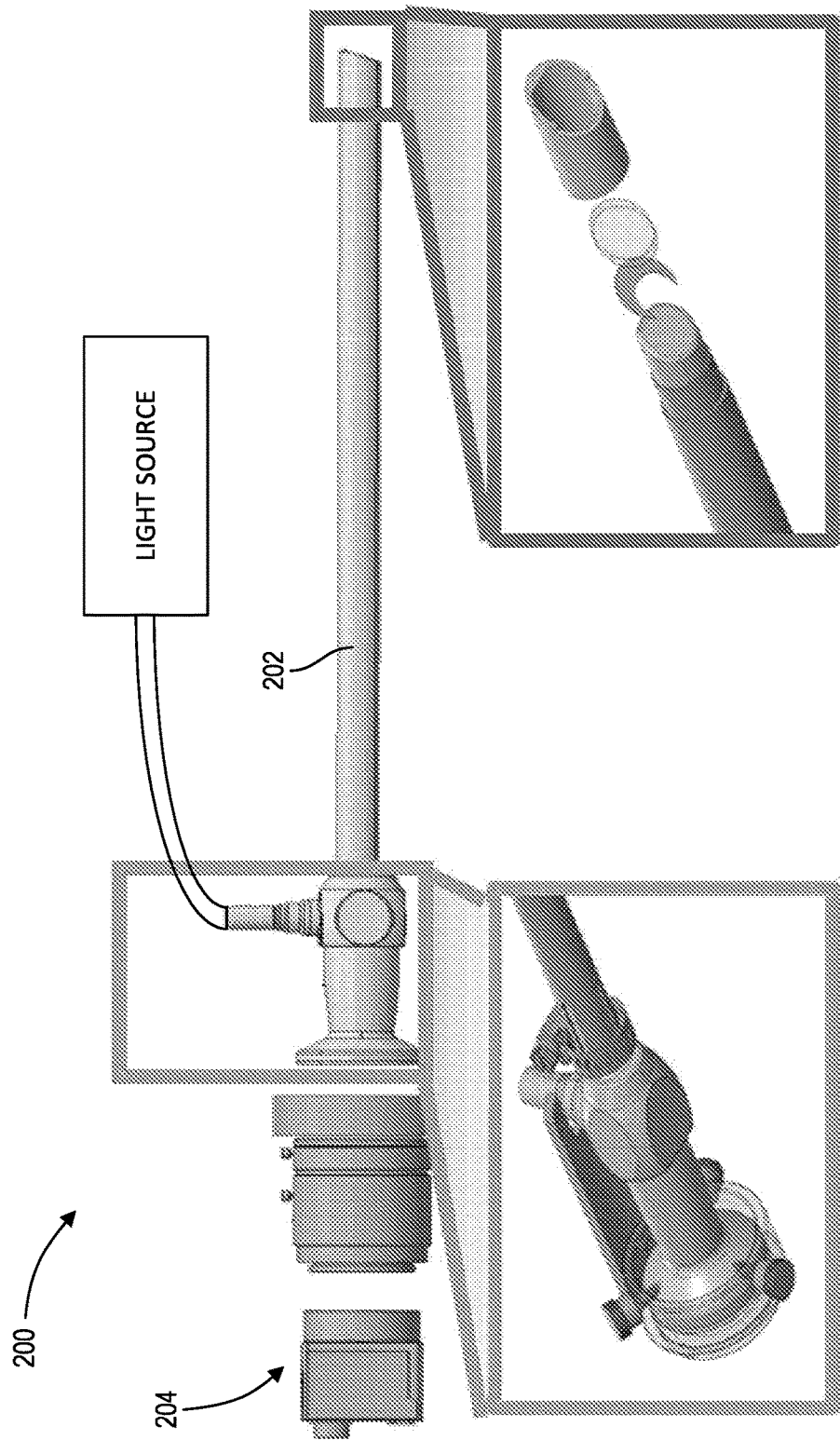
FIG. 2 schematically depicts an implementation of an mPEL device in which a polarization sensitive camera is employed for the detection of the backscattered radiation.

With reference to FIG. 2, in another embodiment, a laparoscopic system 200 includes a tube 202 in which an optical fiber is disposed (not shown in the figure) for receiving light from a light source (not shown in the figure) and transmitting the light from the light source to a target tissue and collecting the light reflected/backscattered from the target tissue. Similar optics as those described in connection with the laparoscope depicted in FIG. 1 can be utilized for directing the illuminating light to the target tissue and collecting reflected/backscattered light and directing the collected light to a detector 204, In this embodiment, the detector 204 can be a polarizing camera (herein also referred to as a polarization sensitive camera). For example, polarizing CCD cameras are currently available that can record simultaneous images in different polarization states. One such polarizing camera is the Blackfly S USB3 camera available from FLIR, Inc. (Arlington, VA). A polarizing CCD camera typically is comprised of four different angled polarizers (90°, 45°, 135° and 0°), which are placed on each pixel. The relationship between two or more of the images captured via the different polarizers permits a calculation of PEL at full frame rate. In this embodiment, the variable waveplate 116 and the polarizer 118 may be omitted.

In yet another alternative, one can use different polarization states of the scattered light from which the PEL image may be calculated. In the prior embodiment, the parallel and perpendicular images are acquired to calculate the PEL image. However, the PEL image may also be calculated from the unpolarized image and the parallel image, the unpolarized image and the perpendicular image, and other image pairs that together contain both parallel and perpendicular polarization information, while at least one contains information exclusive to parallel or perpendicular on its own.

Additionally, while various embodiments exploit the linear parallel and perpendicular polarization of light, in other embodiments circular R and L polarized light may be utilized for implementing the present teachings, but with a lesser degree of bulk signal removal.

Further understanding of various aspects of the present teachings can be obtained by reference to the following Examples.

Examples

The following describes a first-in-human feasibility study, including 10 adult patients who underwent standard staging laparoscopy (SSL) for gastrointestinal malignancy along with PEL. Image frames of all detectable peritoneal lesions underwent analysis. Using Monte Carlo simulations, contrast enhancement based on the color dependence of PEL (mPEL) was assessed.

Sixty-five lesions (56 presumed benign and 9 presumed malignant) from 3 patients represented the study sample. While most lesions were visible under human examination of both SSL and PEL videos, more lesions were apparent using SSL. However, this was likely due to reduced illumination under PEL. When controlling for such effects through direct comparisons of integrated (WLL) vs differential (PEL) polarization laparoscopy images, PEL imaging yielded an over 2-fold Weber contrast enhancement over WLL. Further, enhancements in the discrimination between malignant and benign lesions were achieved by exploiting the PEL color contrast (mPEL) to enhance sensitivity to tissue scattering, influenced primarily by collagen.

The study results indicate that when controlling for the degree of illumination, mPEL may provide improved visualization of metastases.

As noted above, successful treatment of cancers requires optimal selection of treatment modalities. Surgical resection is a common treatment modality for various cancers and is clinically utilized in almost half of all cancer patients. The appropriateness of surgical resection is typically determined by the extent of the cancer (i.e., staging). Despite careful preoperative radiographic and intraoperative evaluation, the accuracy of staging for distant metastases remains poor, as demonstrated by a significant rate of early cancer recurrence in patients who underwent a "complete" operative resection for many types of cancers. It is therefore desirable to develop an imaging system that will enhance the visibility of these occult and presumed small distant metastases, i.e., increase their optical contrast. For abdominal cancers, this would particularly involve the peritoneal cavity.

As discussed herein, differences in the rate of depolarization of linearly polarized incident illumination as detected by a polarization-enhanced laparoscope (PEL) can provide enhanced contrast for changes in collagen fiber organization and cross-section relative to white light laparoscopy (WLL). In various embodiments, collagen organizational changes can be employed using polarization sensitive imaging techniques discussed herein to detect and distinguish lesions.

A PEL system according to an embodiment of the present teachings for collection and analysis of imaging data in this example relied on tissue illumination with linearly polarized white light and detection of light that is polarized along parallel (co-polarized) and perpendicular (cross polarized) orientations relative to the incident illumination. The difference of these two linearly polarized images was considered a PEL image, while their sum was considered the corresponding WLL image, which should in principle be very similar to the images acquired during standard staging laparoscopy (SSL). As indicated above, under PEL imaging the tissue surface is illuminated with linearly polarized white light. Light captured by the camera after being scattered only within the superficial tissue scatters relatively few times and thereby maintains to a large extent its incident polarization providing primarily co-polarized signals. Conversely, light scattered within the deeper tissue layers becomes depolarized, as a result of a multitude of scattering interactions during its longer optical path through tissue before being captured by the camera. This type of scattered light, therefore, contains approximately equal level of co- and cross polarized light relative to the incident illumination. These expected differences in the polarization character of light scattered within the superficial and deeper tissues can be exploited to enhance visualization of the surface signal only. By way of example, this can be achieved via the computation of the difference between the co-polarized ("all" of superficial and "half" of deep) and cross-polarized ("half" of deep) signals:

$$I_\Delta = I_\| - I_\perp \tag{1}$$

$$I_\Delta = \left(I_{surface} + \frac{1}{2}I_{deep}\right) - \left(\frac{1}{2}I_{deep}\right) \quad (2)$$

$$I_\Delta = I_{surface} \quad (3)$$

In various embodiments, this type of polarization-gated imaging captures a light signal with a very short penetration depth of 3 optical depths in scattering media (typically on the order of 100-300 µm). Since the penetration depth of white light exceeds the thickness of peritoneum, this may be advantageous for highlighting changes in scattering properties resulting from the presence of peritoneal metastases, which are primarily present on the peritoneal surface. In addition, the PEL signal increases as linear depolarization (change in the direction of the incident polarization that results from scattering) and retardance (differences in the propagation speed of the light within birefringent media dependent on its polarization) decreases. This results in highlighting of targets, like malignancies, that contain collagen fibers with lower scattering cross section and higher alignment than the surrounding healthy tissue. Finally, PEL imaging with standard RGB cameras can exploit color sensitivity to enhance visualization of features with absorbance contrast such as vasculature, while enabling the acquisition of regular color unpolarized images (provided by the sum of the two orthogonal polarization images).

In various embodiments, mPEL can improve identification of metastases compared to standard laparoscopy during routine abdominal cancer operations based on polarization signatures of peritoneal lesions. Further, in some embodiments, PEL can be used as an adjunct to SSL to provide label-free contrast enhancement of peritoneal metastases.

Methods and Materials

Population

The data discussed herein was obtained from ten adult patients (age>=18 years) who were scheduled to undergo SSL for biopsy-proven malignancy of the gastrointestinal tract at Lahey Hospital in Burlington, MA. Exclusion criteria included pregnancy, BMI>60 kg/m2, severe cardiopulmonary comorbidities, coagulopathy, emergent operation, and vulnerable populations.

System and Device

The system used to obtain the data discussed in this example included a custom-made PEL prototype. The SSL system included an FDA-approved 10-mm 30-degree rigid laparoscope (Olympus EndoEYE, Center Valley, PA) connected to a standard light source (Olympus Evis Exera II CLV-180) and processor (Olympus Evis Exera II CV-180). The PEL prototype (FIG. 1) included a lens rod (Karl Storz Hopkins II 10 mm 30-degree model 26003BA, Tuttlingen, Germany) that had undergone custom modification to include a fused silica optical window to avoid polarization effects exhibited by a conventional sapphire window. The lens rod was connected via a fiber-optical cable to a standard light source (Olympus Evis Exera II CLV-180). Due to the depolarizing effects of the fiber optics, polarization filtering of the illumination had to be conducted at the distal end of the fibers. Therefore, the lens rod was covered by a metal sheath with a cap threaded to the distal end that included a linear polarizing film (Thorlabs LPVISE100-A, Newton, NJ) only covering the illumination aperture but not the camera inlet window (See polarizer 118 depicted in FIG. 1). The arrangement allowed generating linearly polarized illumination.

The resulting reflectance from the abdominal cavity was captured through the aperture of the GRIN lens rod, which was not expected to modify the polarization state of the light. Attached to the proximal end of the lens rod was a mount adapter that connected to an optical assembly to allow for PEL imaging. Within the assembly, image signals were relayed through an electrically tunable liquid crystal variable waveplate (Thorlabs LCC1111T-A) with the slow axis oriented at 45 degrees. Two operating voltages were switching between zero (1.6 V) and half-wave (25 V) retardance for each frame. In this way, a series of alternating images were created that alternated between an image that maintained the original polarization (zero retardance) and an image that rotated the polarization by 90 degrees (half-wave retardance), respectively.

From the variable waveplate, the images traveled through a linear polarizer (Thorlabs LPVISE100-A) that was in line with the illumination polarization to isolate the co- (zero retardance) and cross- (half-wave retardance) polarized components of the collected signal. Subsequently, the images traveled through a varifocal zoom lens (Computar 12-36 mm, Cary, NC) before being captured onto an RGB charge coupled device (CCD) camera with 1920×1200 pixel resolution, at a rate of 27 frames per second, and 12-bit pixel depth (FLIR Blackfly 23S2C-CS, Wilsonville, OR). The switching of the variable waveplate was synchronized with the camera's frame collection utilizing a built-in strobe feature. The series of collected images alternating in polarization state were then processed in real-time to generate a new stream of images, with the PEL image computed as the difference of co- and cross-polarized images and the WLL image computed as their sum. Prior to its use, the device underwent laboratory performance evaluations as well as mechanical, electrical, thermal, chemical, and sterilization safety tests.

Intra-Operative Imaging

Patients underwent SSL evaluation of the abdominal cavity at the beginning of the operation according to best medical practice immediately followed by PEL. During PEL examination, WLL images (I=/I∥+I⊥) and PEL images (IΔ=/I∥−I⊥) were displayed on the operating room monitors. Co- and cross polarized images were separately recorded to allow for post-hoc analyses. Any biopsies of lesions were conducted after completion of PEL under SSL using standard clinical practice. All procedures were performed by a single surgeon (T.S.). After the operation, the recorded videos were analyzed for the effectiveness of illumination of the abdominal cavity and visualization of intra-peritoneal organs along with the clinical safety of the device.

Image Capture and Human Performance Analysis

For quantitative comparison of lesion visibility across each modality, single representative image frames depicting a peritoneal lesion were collected post-hoc from the SSL and the PEL videos by a single surgeon (T.S.). SSL videos were reviewed first. From the videos, any detectable lesion of any of the peritoneal surfaces was captured by a representative still image depicting the lesion. The images were recorded in TIFF format (24-bit RGB, lossless compression). Similarly, PEL videos were separately reviewed, and lesion images were captured providing PEL and WLL images.

Thereafter, the image collections from SSL and PEL modalities were evaluated to identify any lesions seen in both modalities (i.e., WLL images from the PEL device were compared to SSL images based on surrounding anatomic landmarks). A second review of each video was performed to determine whether any lesions noted on the opposing modality could in retrospect be detected. Images of lesions identified during the second review were captured. If a corresponding lesion was not identified, the expected region of the lesion was captured using a similar vantage point as the opposing modality. According to the second review, lesions were classified based on whether they were seen equally with both modalities (i.e., both seen during first review), only seen in retrospect once noted with the other modality (i.e., only noted during second review), or not seen with one modality at all. Further, lesions were classified as "presumed benign" if 1) a biopsy of the lesion was performed and deemed benign or 2) if no biopsy of the lesion was performed and based upon clinical judgement the lesion was considered of low probability to be malignant. "Presumed malignant" lesions were determined based on similar concepts.

Digital Image Processing Analysis

Figures 3A, 3B:
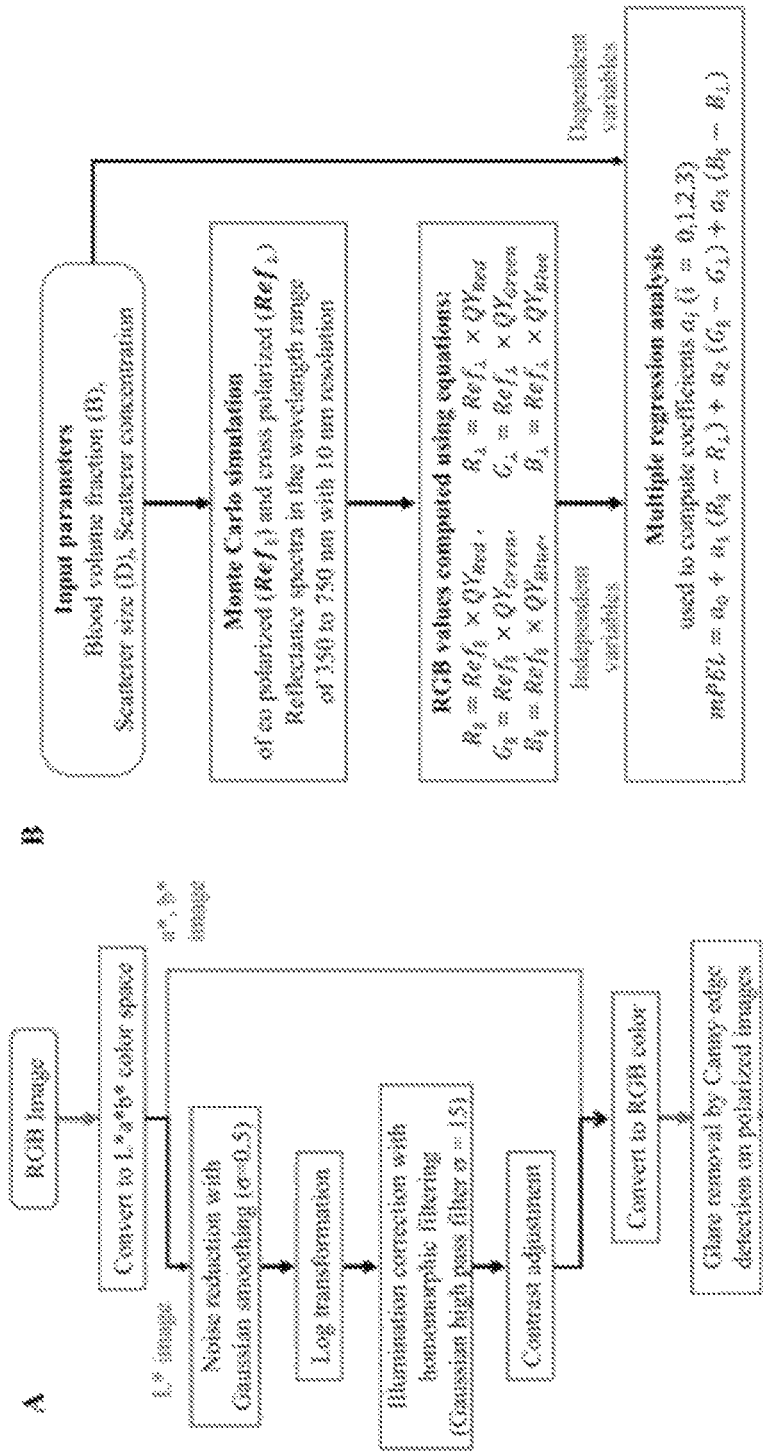
FIG. 3A is a flow chart of an image pre-processing method in accordance with an exemplary embodiment.
FIG. 3B is a flow chart for computing modified PEL using Monte Carlo-based regression analysis in accordance with an exemplary embodiment.

The performance of PEL was subject to issues with image quality, primarily resulting from the reduced illumination power of the device, since essentially half of the light was blocked by the illumination linear polarizer. This was expected to bias the comparison analysis of the prototype to the current clinical standard (i.e., SSL from a fully developed system). To mitigate this bias for any digital analyses, WLL images defined as the sum of co- and cross-polarized images (i.e., unpolarized light images) obtained from the prototype were used in lieu of the SSL images. Since WLL captures both surface and subsurface features, WLL images should be in principle very similar to SSL images. WLL and PEL images used in the analysis were computed respectively as the sum and difference of co- and cross-polarized signals:

$$WLL = I_{surface} + I_{deep} = (R_\| + R_\perp) + (G_\| + G_\perp) + (B_\| + B_\perp) \quad (4)$$

$$PEL = I_{surface} = (R_\| - R_\perp) + (G_\| - G_\perp) + (B_\| - B_\perp) \quad (5)$$

where R, G, B refer to red, green, and blue components of white light, respectively, and the $\|$, $\perp$ subscripts refer to co- and cross-polarized components of light, respectively. All WLL and PEL study images were pre-processed to reduce detector noise and to enhance contrast using MATLAB software version R2019a (MathWorks, Natick, MA) (FIG. 3A). Original images were converted from RGB to Lab color space where image L contained luminosity and images a and b contained information of green-red and blue-yellow spaces respectively. The following processing protocol on L was applied, while images a and b were unmodified: Gaussian smoothing to reduce detector noise (2-D Gaussian smoothing kernel with standard deviation of 0.5), homomorphic filtering to address non-uniform illumination artefacts (low frequency bands were filtered out from log-transformed images using a Gaussian filter with standard deviation of 15), and contrast adjustment (saturating the bottom 1% and the top 1% of all pixel values). The resulting Lab color space image was converted back to RGB color space. Further, glare regions were identified based on a Canny edge detection algorithm applied to pixels representing the upper 0.5th intensity percentile of the co-polarized images and the lowest 0.5th intensity percentile of the corresponding cross-polarized images and removed. Regions of interest (ROIs) were manually outlined on WLL and PEL images containing the visible borders of the lesions. In case a lesion was only visible in the opposing modality, the expected region of the lesion based on anatomic landmarks was used as ROI. Mean intensity measures were recorded within the ROI. Weber contrast was computed accounting for the entire surrounding image background other than the ROI, where Weber contrast (Cw) as a function of intensity in the ROI (If) and intensity of the entire background (Ib) was defined as:

$$C_w = \frac{I_f - I_b}{I_b} \quad (6)$$

Computation of Modified PEL Through Monte Carlo-Based Regression Analysis

Since the extent of backscattering under PEL was expected to differ at various wavelengths (colors), a model was developed to account for this wavelength dependence to further augment the sensitivity of PEL to scattering changes, and specifically to the scattering power. In principle, the tissue scattering coefficient can be approximated by $\sim\lambda^{-b}$, where $\lambda$ is wavelength, and b is defined as the scattering power. For this purpose, a Monte Carlo-based regression analysis was performed to extract the general scattering power dependence on the three RGB color channel intensities of the PEL images, based on a weighted linear equation. Since scattering cross section of tumor tissue is generally lower than that of the surrounding tissue, and scattering power is inversely proportional to scattering cross section, lesions were expected to exhibit a greater scattering power than the background tissue resulting in a positive Weber contrast.

With reference to FIG. 3B, polarization-sensitive Monte Carlo simulations for a single layered tissue model written in C were used to compute polarized light propagation in tissue with similar optical properties to those of peritoneal tissue. The code simulated Mie theory scattering for spherical particles and tracked the polarization direction of light using the Stokes vector. The optical depth of the medium was limited to 20, since the WLL signal saturates for larger thicknesses. Here, optical depth was defined as $\tau = (\mu_a + \mu_s)D$, with D representing the geometrical thickness. The Monte Carlo simulation generated a lookup table for reflectance intensities for a range of scattering coefficients (10 cm$^{-1}$ to 35 cm$^{-1}$ with 5 equal steps), scattering cross sections (0.5 to 8 µm$^2$ with a step size of 0.5 µm$^2$), and blood volume fractions (0.4 to 0.9% with a step size of 0.1%) that are typically encountered in soft tissue under different pathological conditions. Absorption coefficients were estimated by assuming a hemoglobin concentration in blood of 15 g/dL. Extinction coefficients of hemoglobin ($\epsilon$Hb) were obtained from the public domain. An anisotropy coefficient of 0.9 for the tissue was used in the simulations. A refractive index of 1.35 and 1.42 were fixed for the surrounding tissue and scatterers in the simulations. Finally, RGB values were obtained from the reflectance spectra by considering detector efficiency profiles (QYred, QYgreen, QYblue) of the digital camera in the wavelength range of 350 to 750 nm. Multiple regression analysis with simulated data sets, established a regression equation for tissue scattering power, as $$mPEL = a_0 + a_1(R_\| - R_\perp) + a_2(G_\| - G_\perp) + a_3(B_\| - B_\perp) \quad (7)$$

The regression coefficients at (i=0, 1, 2, 3) were estimated in MATLAB using the inbuilt function 'regress' and they reflected the contributions of RGB values to scattering power.

2D Variance of Collagen Fibers in Biopsied Lesions

Hematoxylin and eosin-stained histology slides were obtained from all lesions that were biopsied during the operation and that were included in the analysis (3 malignant and 2 benign). The slides underwent imaging using a laser scanning confocal microscope (Leica TCS SP8, Wetzlar, Germany) equipped with Ti:sapphire laser (Spectra Physics, Mountain View, CA). Second harmonic generation (SHG) images were acquired with an excitation wavelength of 860 nm and recorded at 425±25 nm using a non-descanned detector. Laser light was focused on the sample using a water immersion 25× objective (0.95 numerical aperture) to provide a sufficient field of view of 465×465 $\mu m^2$.

The biopsy samples had 8 to 10 µm thickness and they were imaged along a z stack with a 2 µm step. Three ROIs from each lesion were imaged. The localized 2D directional variance of the collagen from SHG images were computed using a 2D variance algorithm described in Quinn K P, Georgakoudi I (2013) Rapid quantification of pixel-wise fiber orientation data in micrographs. J Biomed Opt 18:046003, which is herein incorporated by reference in its entirety. The algorithm segmented the fiber-only regions based on Otsu thresholding and the orientation of the fibers were estimated based on a weighted vector sum approach. The distribution in the azimuthal angles was used to estimate the 2D variance of the collagen in the biopsy tissues. The area fraction of the collagen was estimated as the ratio of the pixels within the segmented fiber-only region to the pixels within the entire field.

Statistical Analysis

Descriptive statistics were obtained, and bivariate analyses were used to assess the relationship between lesion classification and the image signal signature. Mean signal intensities and Weber contrast of lesions in the WLL, PEL, and mPEL images were compared using one-way ANOVA with Tukey's HSD post-hoc tests. The difference in mean intensities and Weber contrast of benign and malignant lesions under WLL, PEL, and mPEL were compared using two sample t-tests. Statistical significance was considered for $p<0.05$. All statistical analyses were performed using MATLAB.

Results

Study Demographic

Ten patients underwent staging laparoscopy for gastrointestinal malignancies. Of these patients, 4 were subsequently excluded due to imaging failures (research device not providing adequate imaging due to condensation of the front-end optical window during the operation (n=3), research device failed pre-procedure tests (n=1)). Therefore 6 patients were included in the analysis. The study group consisted of 3 patients with pancreatic ductal adenocarcinoma, 2 patients with gastric adenocarcinoma, and 1 patient with jejunal adenocarcinoma. This included 3 men and 3 women, representing 5 white and 1 black individual. The median age was 77 years (range 64 to 96 years). Each patient underwent between 1 and 3 biopsies of clinically suspicious appearing peritoneal lesions. One of the 6 patients had biopsies confirming the presence of peritoneal metastases. The remaining 5 patients did not show detectable evidence of metastatic disease at the time of operation, nor any radiographic evidence of metastases within 6 months of clinical follow-up.

Device Performance and Image Quality Selection

While PEL images were as expected darker than SSL images, the subjective determination of the effectiveness of illumination of the abdominal cavity and visualization of intra-peritoneal organs demonstrated good visualization in two patients (median image pixel intensity 23.3 (range 7.5 to 42.9), including the patient with peritoneal metastases), moderate visualization in one patient (median image pixel intensity 6.1 (range 0.0 to 7.8)), and poor visualization in three patients (median image pixel intensity 0.0 (range 0.0 to 1.8)).

Data from the latter patients were excluded. Besides limited illumination using a standard light source, fogging of the window on the distal cap was at times an issue, but was well controlled in the 6 study patients. Issues with coregistration of the co- and cross-polarized images, which were a result of the temporal difference in capturing the two images, resulted at times in mild flickering of the PEL video and false borders around the lesion. This was particularly present if the laparoscope moved fast. The safety of the device was good without any research associated complications. It was very well integrated into the operating room environment.

Sixty-five lesions from three patients represented the study sample (9 presumed malignant lesions, 56 presumed benign lesions). Among them, 5 lesions were biopsied and 3 of the biopsied lesions were confirmed as malignant (all 3 from one patient) and 2 of them as benign (from two patients).

Clinical Lesion Detection by the Surgeon

Figure 4:
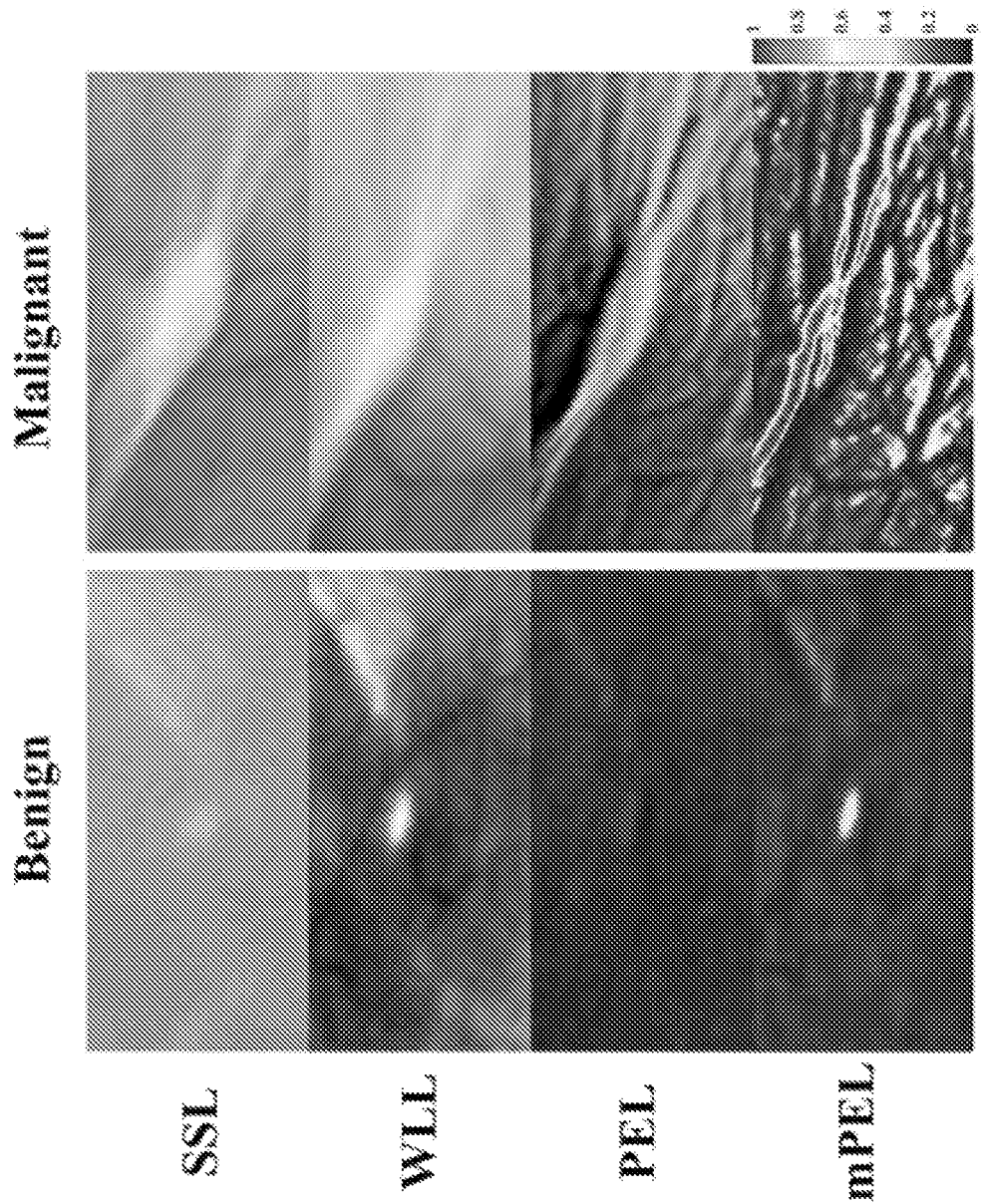
FIG. 4 depicts SSL, WLL, PEL, and mPEL images of biopsy confirmed parietal peritoneal metastasis and benign lesions.

Of the 65 study lesions identified post-hoc: a) 18 (28%) were better seen by the surgeon on SSL (lesion was noted on PEL only after location was identified on SSL (n=7) or was not seen on PEL at all (n=11)), b) 35 (54%) were equally visible with both modalities, and c) 12 (18%) lesions were better seen on PEL (lesion was noted on SSL only after location was identified on PEL (n=10) or was not seen on SSL at all (n=2)) (FIG. 9). Thus, based on visual inspection lesions were visualized with greater sensitivity using SSL than PEL. Examples of the optical appearance of these images are shown in FIG. 4.

Computation of mPEL

To take advantage of color dependent contrast that may enhance sensitivity to collagen structural changes under PEL, Monte Carlo simulations led to the following relationship to optimize the correlation between the potential range of PEL signals detected in each of the camera's RGB channels and the tissue scattering power:

$$mPEL = 0.4705 - 0.0073(R_\parallel - R_\perp) - 0.0039(G_\parallel - G_\perp) + 0.1104(B_\parallel - B_\perp) \tag{8}$$

Figure 5:
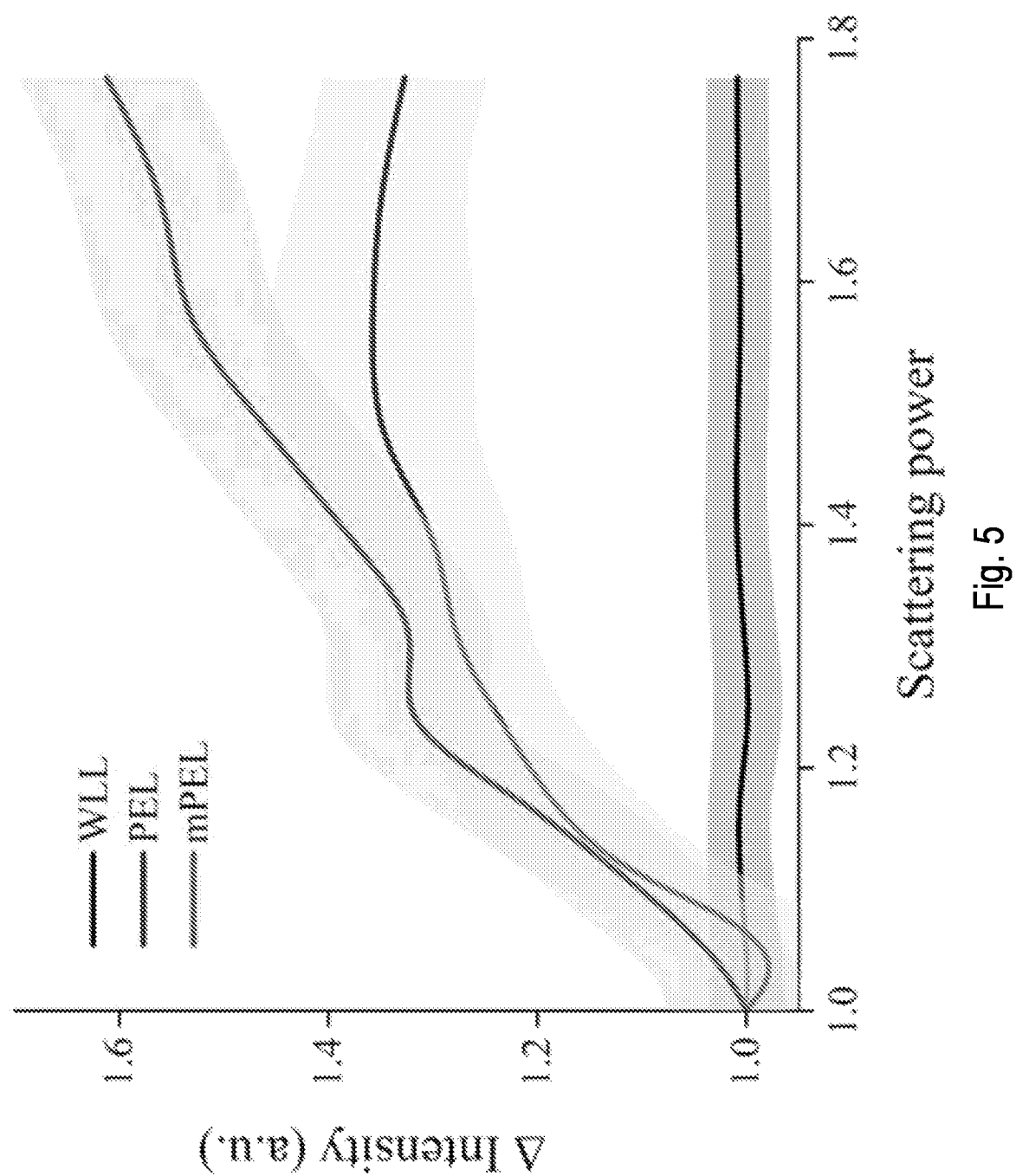
FIG. 5 depicts Monte Carlo simulations of WLL, Pel, and mPEL for a range of scattering powers encountered in peritoneal tissue

This equation was used to create images that represented a modification from the original PEL images (i.e., mPEL). FIG. 5 shows Monte Carlo simulations of the relative change in the reflected light intensity as a function of scattering power under WLL, PEL, and mPEL imaging. It was observed that while WLL is independent of scattering power, PEL shows a strong dependence on scattering power, while mPEL exhibits an even stronger dependence than PEL.

Digital Lesion Detection

Figures 6A, 6B:
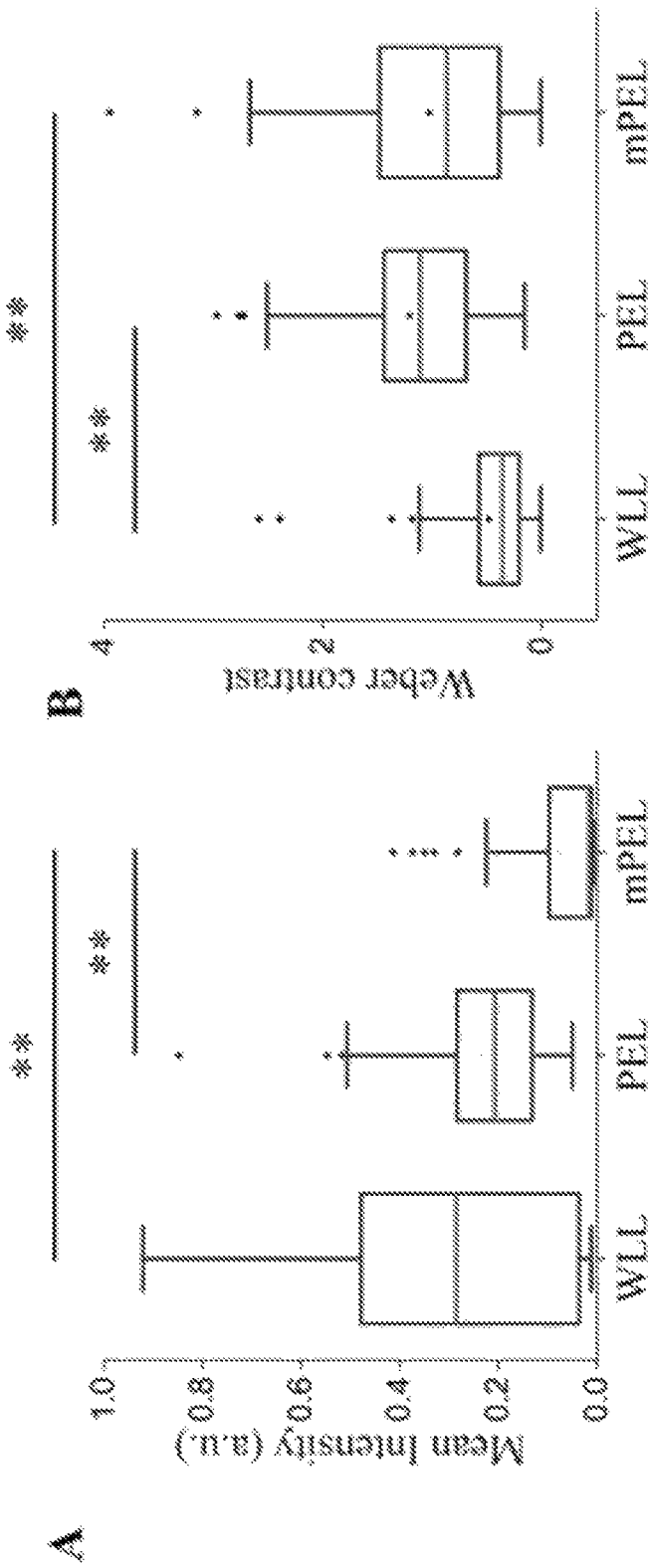
FIG. 6A depicts mean ROI intensity for a study of 65 lesions.
FIG. 6B depicts Weber contrast for a study of 65 lesions

Assessing all 65 study lesions, the mean ROI total signal intensity (sum of red, blue, and green channels) under PEL and mPEL was 1.3-fold and 3.8-fold lower compared to WLL, respectively (FIG. 6A). The Tukey's post hoc test confirmed that there was significant difference between the mean intensity of WLL and mPEL images ($p<0.001$), but the difference between WLL and PEL was insignificant ($p=0.186$). Yet, due to the overproportionate darker background on PEL, the corresponding mean Weber contrast under PEL was 2.5-fold greater compared to WLL, suggesting the potential for improved lesion detection using PEL when controlled for the degree of illumination ($p<0.001$). Upon exploiting the color-dependence of PEL, mPEL provided 2.1-fold greater Weber contrast compared to WLL ($p<0.001$, FIG. 6B).

Digital Lesion Classification

Figures 7A, 7B:
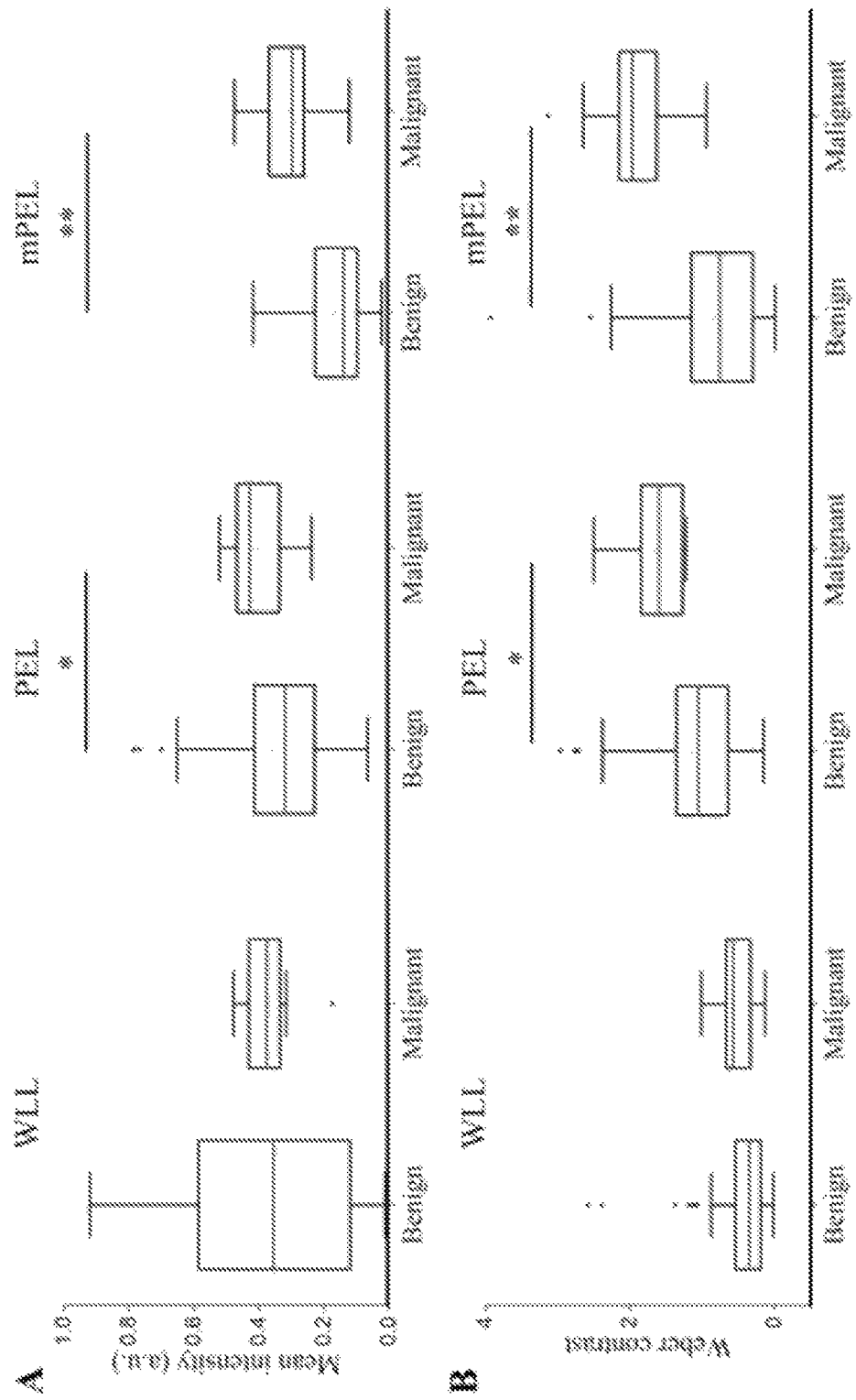
FIG. 7A depicts box plots of mean intensities of presumed benign lesions compared to presumed malignant lesions.
FIG. 7B depicts box plots of Weber contrast of presumed benign lesions compared to presumed malignant lesions.

There was no measurable difference in ROI intensity when comparing presumed benign lesions ($n=56$) to presumed malignant lesions ($n=9$) observed under WLL ($p=0.910$). However, PEL and mPEL were able to provide a 1.1-fold and 1.8-fold greater ROI intensity in presumed malignant lesions compared to presumed benign lesions, respectively (PEL $p=0.037$, mPEL $p<0.001$, FIG. 7A). The findings indicate that malignant lesions are characterized by a higher scattering power than benign lesions (mean malignant mPEL intensity=$0.30\pm0.10$; mean benign mPEL intensity=$0.16\pm0.09$).

It is theoretically possible that these findings might be due to differences in illumination, since all presumed malignant lesions came from a single patient. Nevertheless, Weber contrast confirmed the same findings making illumination differences as the cause of the findings less likely. Specifically, the Weber contrast of PEL and mPEL images was 1.4-fold and 2.3-fold greater than WLL images for malignant compared to benign lesions, respectively (PEL $p=0.031$, mPEL $p<0.001$, FIG. 7B).

Correlation of mPEL to Collagen Structure

To better understand the etiology of the augmented signal between presumed malignant lesions and presumed benign lesions provided by mPEL, microarchitectural changes in the collagen organization of benign and malignant lesions were assessed in all available biopsy samples from this study. Specifically, SHG images were acquired from 2 benign and 3 malignant lesions (FIGS. 8A and 8B). Three ROIs from each benign and malignant lesion were imaged. The analysis results showed that there was a lower collagen volume fraction in malignant lesions compared to the benign ones (FIG. 8C). Further, the directional variance of the collagen fibers within the malignant lesions was found to be lower than that of the benign lesions (FIG. 8D).

The above examples demonstrate that laparoscopy using the designed PEL prototype can be performed safely in patients undergoing staging laparoscopy. Reasonable measurements on the visualization of peritoneal metastases under PEL and mPEL in comparison to WLL/SSL were achieved (See, e.g., FIG. 4).

Subjective detection of peritoneal lesions by a human examiner was seemingly overall worse with PEL compared to SSL. These differences were likely due to significantly darker illumination under PEL compared to SSL, supported by the findings of the digital analysis demonstrating lower lesion intensity values under PEL. However, using Weber contrast as means for digitally controlling for the degree of illumination, improved lesion detection was noted with a 2.5-fold increase in contrast and therefore potential for better visualization of any lesion using PEL compared to WLL.

Without being limited to any particular theory, this enhancement occurs because under PEL imaging the background is suppressed at higher levels than the signal emanating from regions containing superficial lesions. The effect was similar when using mPEL providing a 2.1-fold increase. The results suggest that with future improvement in illumination, PEL and mPEL should be able to significantly enhance contrast to theoretically allow for a human to better recognize peritoneal lesions In classifying peritoneal lesions, PEL also seemed to perform better than WLL. It provided a 3-fold greater Weber contrast for malignant lesions compared to benign lesions. mPEL, with its wavelength-dependent measure, seemed to even further augment this difference (3.6-fold increase).

Hence, the present teachings can be used to achieve enhanced sensitivity and specificity for identifying potentially occult malignant lesions, supporting their usefulness for staging laparoscopy.

The enhanced PEL/mPEL contrast for malignant versus benign peritoneal lesions is consistent with the changes in collagen content and organization observed in fixed sections from benign and malignant biopsied tissues. Malignant tissues, including peritoneal metastases, harbor a lower volume fraction of more highly aligned collagen fibers compared to healthy tissues. These changes are expected to lead to a decrease in scattering cross section, and a subsequent reduction in the depolarization of backscattered light and corresponding increase in the PEL signal. Under mPEL, this phenomenon is enhanced further to achieve an optimized correlation of the mPEL signal to scattering power.

A wide range of cancer tissues are less depolarizing than corresponding healthy tissues. Mueller-matrix polarimetric imaging systems that characterize fully the polarization-dependent interactions between light and tissue are likely to yield the most sensitive assessments of tissue scattering changes. However, the instrumentation, image acquisition, and processing time required for the 16 needed polarization-resolved images limit integration into a real-time surgical guidance workflow, even with recent advances that decrease the acquisition frame rate to as low as 1 s.

Faster implementations of simpler polarized systems exist, including those which are based on differential polarization. For example, linear, cross-polarized imaging has been used to visualize collagen disruption at the margins of skin cancers during resection. Circularly polarized light-based systems were also considered to image subsurface tissue layers, since the rate of depolarization of circularly polarized light is slower than that of linearly polarized light. However, since peritoneal lesions are typically around the thin (~5 μm) peritoneal lining, linear polarization gating, like PEL, is more suitable for enhanced visualization of superficial changes in the collagen structure. While RGB contrast has been exploited in differential polarization systems to enhance contrast for visualizing blood vessels, and in cross-polarized images to enhance contrast from collagen in deeper layers, in the context of laparoscopy, color sensitivity of differentially polarized light enhances contrast to superficial collagen changes.

Image quality in some of the images may have decreased due to poor illumination. Images with very poor illumination were excluded, presumably without introducing large selection bias. Limitation in other forms of image quality as a result of using a prototype were controlled for in the digital analysis by using WLL rather than SSL as a comparison. Patient sample size was limited, but a reasonable number of lesions were imaged and analyzed. Analyses were done mostly under a presumed pathology status given the limited number of biopsy proven pathology among all lesions. This provides some potential measurement bias for the classification task. Nevertheless, it is noted that the patients who were assigned with "presumed" labels correlated with the patients' clinical outcome (i.e., none of the patients with presumed benign lesions had radiographic cancer progression within 6 months after the operation and the only patients with presumed malignant lesions has three lesions that were biopsy-proven metastases).

PEL and mPEL have potential to improve detection of peritoneal lesions and to help differentiate benign from malignant lesions. This contrast enhancement likely arises from the changes in collagen content and organization that are present in peritoneal metastatic lesions. Improved understanding of the range of collagen organization changes that may be associated with the primary tumor origin and the impact of such variations on PEL/mPEL vs SSL images would be important for optimizing detection. The ease of integration of PEL/mPEL into routine laparoscopic imaging facilitates the incorporation of these techniques into clinical practice.

While various embodiments have been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A method of laparoscopic, thoracoscopic, or endoscopic examination of a target tissue region, comprising:
    illuminating a target tissue region with illuminating radiation having a first defined polarization and having a plurality of wavelengths,
    detecting radiation backscattered from the illuminated target tissue in response to illumination by said illuminating radiation and generating a plurality of detection signals each corresponding to one of said wavelengths,
    applying wavelength-dependent weighting factors to said detection signals to generate a plurality of weighted detection signals, and
    utilizing said weighted detection signals to compute an image of the target tissue,
    wherein the step of detecting the backscattered radiation at each of said wavelengths comprises generating a first detection signal corresponding to a polarization of the backscattered radiation parallel to said first polarization and a second detection signal corresponding to a second polarization of the backscattered radiation perpendicular to said first polarization.

2. The method of claim 1, further comprising utilizing said image to assess said target tissue for presence of a malignant lesion.

3. The method of claim 1, further comprising utilizing said weighted detection signals to compute a scattering power of said target tissue.

4. The method of claim 3, further comprising utilizing said computed scattering power to assess said target tissue for presence of a malignant lesion.

5. The method of claim 4, further comprising identifying a lesion as a malignant lesion, for which said scattering power is greater than a predefined threshold.

6. The method of claim 1, further comprising obtaining said wavelength-dependent weighing factors based on any of machine learning or Monte Carlo simulation.

7. The method of claim 1, further comprising processing said first and second detection signals to generate, for each of said wavelengths, a surface signal associated with a superficial portion of the illuminated target tissue.

8. The method of claim 7, further comprising utilizing said surface signals associated with said wavelengths to compute a scattering power of the superficial portion of the target tissue.

9. The method of claim 8, wherein said scattering power is computed as a weighted average of the surface signals associated with said wavelengths.

10. The method of claim 8, wherein a weighting factor corresponding to each of said wavelength-dependent surface signals is computed using multiple regression of Monte Carlo simulated value.

11. A method of laparoscopic, thoracoscopic, or endoscopic examination of a target tissue region, comprising:
    illuminating a target tissue region with illuminating radiation having a first defined polarization and having a plurality of wavelengths,
    detecting radiation backscattered from the illuminated target tissue in response to illumination by said illuminating radiation and generating a plurality of detection signals each corresponding to one of said wavelengths,
    applying wavelength-dependent weighting factors to said detection signals to generate a plurality of weighted detection signals,
    utilizing said weighted detection signals to generate an indicator indicating whether a malignant lesion is present in the target tissue region,
    wherein the step of detecting the backscattered radiation at each of said wavelengths comprises generating a first detection signal corresponding to a polarization of the backscattered radiation parallel to said first polarization and a second detection signal corresponding to a second polarization of the backscattered radiation perpendicular to said first polarization.

12. The method of claim 11, wherein said indicator comprises a scattering power of the target tissue.

13. The method of claim 11, wherein said scattering power is computed as a weighted average of the detection signals at said plurality of wavelengths.

14. The method of claim 11, further comprising identifying a lesion as a malignant lesion when said scattering power is greater than a predefined threshold.

15. The method of claim 11, further comprising processing said first and second detection signals to generate, for each of said wavelengths, a surface signal associated with a superficial portion of the illuminated target tissue.

16. The method of claim 15, wherein the step of processing the first and second detection signals comprises subtracting, for each of said wavelengths, the second signal from the first signal to generate said surface signal.

17. The method of claim 16, further comprising utilizing said surface signals associated with said wavelengths to compute a scattering power of the superficial portion of the target tissue.

18. The method of claim 17, wherein said scattering power is computed as a weighted average of the surface signals associated with said wavelengths.

\* \* \* \* \*